United States Patent
Rozenberg et al.

(10) Patent No.: US 7,763,177 B2
(45) Date of Patent: Jul. 27, 2010

(54) SYSTEM AND METHOD FOR ULTRASONIC CLEANING OF ULTRAVIOLET DISINFECTION SYSTEM

(75) Inventors: Ytzhak Rozenberg, Ramat Gan (IL); Valery Kaluzhsky, Kiryat Gat (IL); Uri Levy, Rehovot (IL); Avi Levin, Yehud (IL)

(73) Assignee: Atlantium Technologies Ltd., Beit-Shemesh (IL)

( * ) Notice: Subject to any disclaimer, the term of this patent is extended or adjusted under 35 U.S.C. 154(b) by 0 days.

(21) Appl. No.: 11/976,731

(22) Filed: Oct. 26, 2007

(65) Prior Publication Data

US 2008/0105625 A1 May 8, 2008

Related U.S. Application Data (60) Provisional application No. 60/854,431, filed on Oct. 26, 2006.

(51) Int. Cl.
*C02F 1/32* (2006.01)
(52) U.S. Cl. ............ 210/748.11; 210/199; 210/748.02
(58) Field of Classification Search ............ 210/748, 210/748.11, 748.02, 199; 250/436, 435
See application file for complete search history.

(56) References Cited

U.S. PATENT DOCUMENTS

| | | | | |
|---|---|---|---|---|
| 4,728,368 | A | * | 3/1988 | Pedziwiatr ............... 134/1 |
| 5,123,433 | A | * | 6/1992 | Fridsma et al. .......... 134/104.1 |
| 5,130,031 | A | * | 7/1992 | Johnston .................. 210/748 |
| 5,539,209 | A | * | 7/1996 | Maarschalkerweerd ..... 250/436 |
| H1568 | H | * | 8/1996 | Huang et al. ............. 210/748 |
| 5,942,110 | A | * | 8/1999 | Norris .................... 210/198.1 |
| RE38,130 | E | * | 6/2003 | Adams .................... 422/186.3 |
| 6,707,048 | B2 | * | 3/2004 | Hallett et al. ............. 250/431 |
| 2004/0065603 | A1 | * | 4/2004 | Grimwood ............... 210/143 |
| 2004/0154988 | A1 | * | 8/2004 | Sheets, Sr. ............... 210/718 |

FOREIGN PATENT DOCUMENTS

JP 401299693 A * 12/1988

* cited by examiner

*Primary Examiner*—Walter D Griffin
*Assistant Examiner*—Cameron J Allen
(74) *Attorney, Agent, or Firm*—Pearl Cohen Zedek Latzer, LLP (57) ABSTRACT

Some demonstrative embodiments of the invention may include a liquid disinfection system having built-in cleaning and deposit prevention capabilities. The system may include a conduit to carry a flowing liquid to be disinfected, an illumination source and an ultrasonic cleaning unit mounted on an external surface of the conduit.

10 Claims, 8 Drawing Sheets

SYSTEM AND METHOD FOR ULTRASONIC CLEANING OF ULTRAVIOLET DISINFECTION SYSTEM

CROSS REFERENCE TO RELATED APPLICATIONS

This application claims the benefit of U.S. Provisional Application No. 60/854,431, filed on Oct. 26, 2006 which is incorporated in its entirety herein by reference.

BACKGROUND OF INVENTION

Disinfection systems using ultraviolet (UV) radiation have been long known. One of the significant problems with these disinfecting systems is the fact that materials within the aqueous systems or media being treated may deposit on the interior surface of the reactor and hence may reduce the effectiveness of UV treatment taking place within the reactor.

A variety of approaches have been provided to overcome this problem. A common approach has been to shut down the reactor after a period of operation to permit mechanical removal, cleaning and/or replacement of the dirty parts. This is an undesirable, expensive and time-consuming procedure. Another approach has been to use chemicals for cleaning the reactor. The use of chemicals for cleaning, which also requires interrupting the disinfection operation, is most undesirable for environmental considerations. An integral and efficient solution which may not interrupt the disinfection is highly required.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

disinfector according to some demonstrative embodiments of the invention.

It will be appreciated that for simplicity and clarity of illustration, elements shown in the drawings have not necessarily been drawn accurately or to scale. For example, the dimensions of some of the elements may be exaggerated relative to other elements for clarity. Further, where considered appropriate, reference numerals may be repeated among the drawings to indicate corresponding or analogous elements. Moreover, some of the blocks depicted in the drawings may be combined into a single function.

DETAILED DESCRIPTION OF EMBODIMENTS OF THE INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and circuits may not have been described in detail so as not to obscure the present invention.

Some demonstrative embodiments of the invention include a cleaning system to clean various UV disinfection systems, as described in detail below. It will be appreciated that the liquid disinfection process may include inactivation or removal of any organism, bacteria, microorganism, being, creature, microbe, germ, virus, organic contaminator, non-organic contaminator, oxidizeable toxic or contaminator; any cumulative noxious species of biological or chemical origin; any oxidizing particle, fragment or element, e.g., Hydrogen peroxide or Titanium dioxide, intended to oxidize a contaminator and/or the like.

In some demonstrative embodiments of the invention, the disinfection system may include a conduit, for example, a reactor, a vessel, a chamber, e.g., an elongated chamber, to carry the liquid. The conduit may have an inlet to receive the liquid and an outlet to discharge the liquid. The system may also include at least one external or liquid immersed illumination source to illuminate the conduit with light. Some demonstrative embodiments of the invention may refer to using ultraviolet (UV) light to disinfect the liquid and/or to oxidize particles within the liquid. However, it will be appreciated by those skilled in the art, that in other embodiments of the invention, light of any other suitable spectrum may be used.

Embodiments of the present invention are directed to a system and method for cleaning interior surfaces of disinfection systems. According to some embodiments of the present invention, an ultrasonic system may be used in order to prevent the creation of deposit on the interior surfaces of the reactor by generating ultrasonic cavitations on the surfaces.

Embodiments of the present invention make use of ultrasonic technology. Ultrasonic cleaning is powered by ultrasonic wave energy. When an ultrasonic wave is projected in liquid, negative pressure is created and causes the liquid to "fracture", a process known as cavitation. Cavitation creates bubbles that oscillate in the projected ultrasonic waves. As the ultrasonic waves continue, these bubbles grow larger and become very unstable, eventually collapsing in a violent implosion. The implosions radiate high-powered shockwaves that dissipate repeatedly at a rate of 25,000~30,000 times per second. Additionally, the implosion of cavitation bubbles creates high temperatures and high pressures. Such Cavitations may be use for ultrasonic cleaning and deposit prevention as described in detail with reference to embodiments of the present invention.

Figure 1:
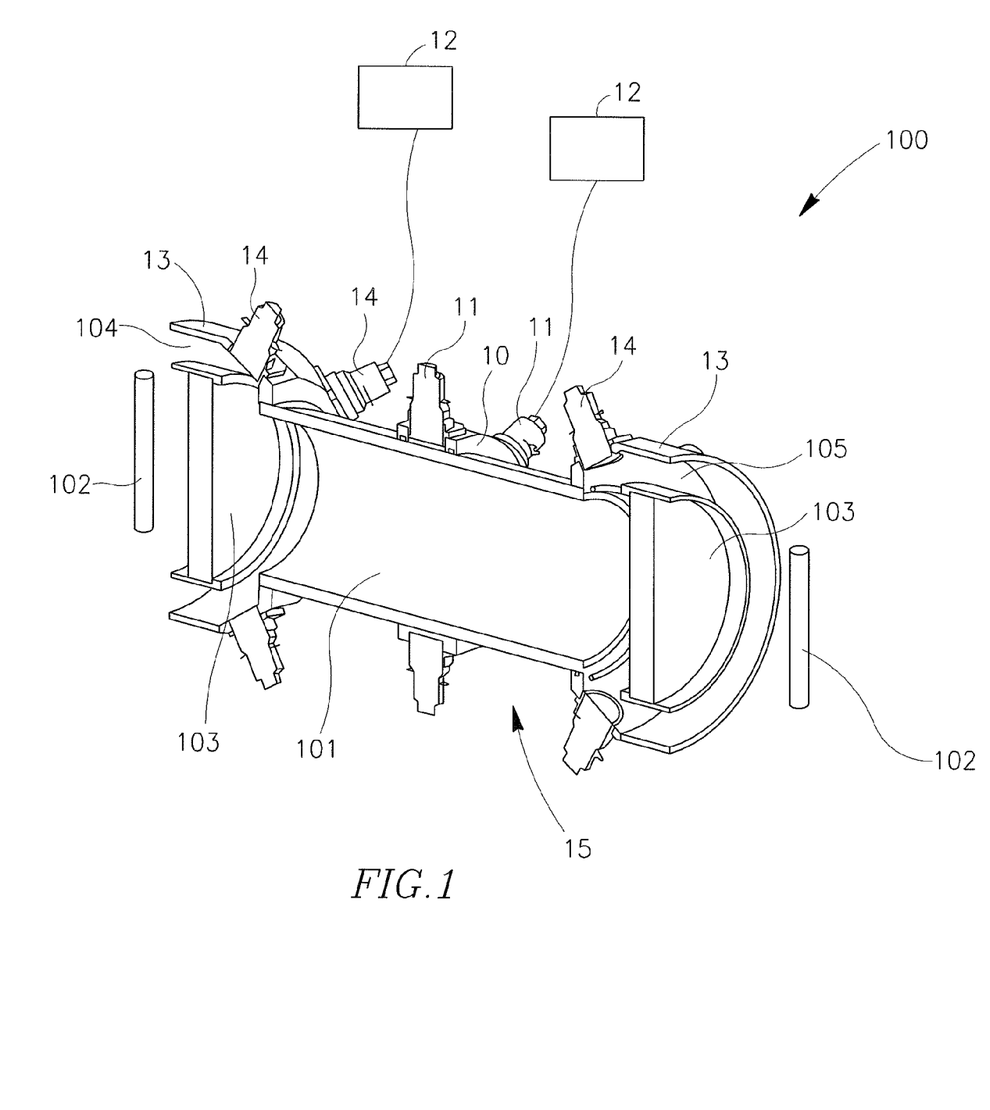
FIG. 1 is a longitudinal cross section of an exemplary disinfection system having cleaning and deposit prevention capabilities according to some demonstrative embodiments of the invention.
Figure 2:
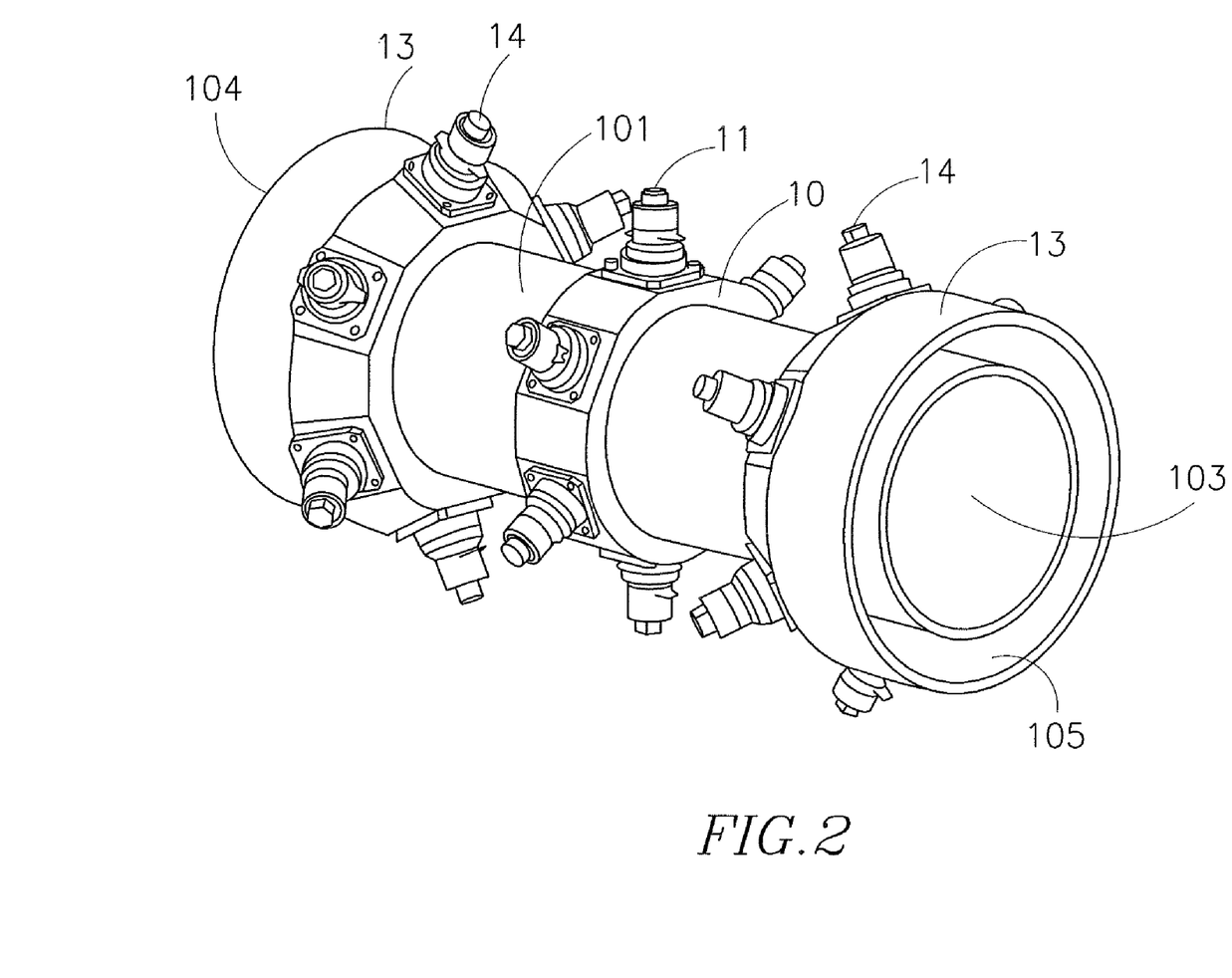
FIG. 2 is an illustration of a side view of the disinfector described in FIG. 1 according to some embodiments of the present invention.

Reference is now made to FIG. 1, which is a longitudinal cross section of a disinfector according to some demonstrative embodiments of the invention. Reference is additionally made to FIG. 2, which conceptually illustrates a side view of the disinfector described in FIG. 1 according to embodiments of the invention.

According to some demonstrative embodiments of the invention, a disinfection system 100 which may be, for example, a hydro-optic reactor may include a reaction chamber, tube or conduit 101, which may be cylindrically formed, and may be used to carry flowing liquid to be disinfected. Disinfection system 100 may include one or more external illumination sources 102 to illuminate and to disinfect the liquid within conduit 101. Conduit 101 may have an inlet 104 to receive the liquid, and an outlet 105 to discharge the liquid. Conduit 101 may be made, at least partially, of a transparent material, such as quartz. Disinfection system 100 may include one or more windows 103 which may be made of a transparent material, such as quartz and may be located at one or more ends of conduit 101, proximate to illumination source 102.

According to some embodiments of the invention, illumination source 102 may be directed to illuminate the liquid within conduit 101 via window 103 with light having a spatial light intensity distribution. The water within the conduit 101 may act as a waveguide, through which the UV rays are directed. The quartz tube may act as both a clear water channel and an effective light trap which maximizes internal reflection. By maximizing internal reflection, a homogeneous and uniform distribution of the UV light is achieved throughout the reactor.

According to some embodiments of the invention, disinfection system 100 may include an ultrasonic cleaning system 15 to prevent, decrease or treat deposit formation on various elements, such as, for example, the interior surface of conduit 1001 or windows 103 as described in detail below with reference to embodiments of the present invention.

Although the invention is not limited in this respect, cleaning system 15 may include one or more cleaning units and one or more ultrasound generators 12. The cleaning units may include one or more central ultrasonic chambers 10 and one or more side ultrasonic chambers 13.

According to some embodiments of the invention, central ultrasonic chamber 10 may be hermetically installed on, mounted on, connected to or attached to the external surface of conduit 101. The number of central chambers 10 mounted on conduit 101 may depend on the length of conduit 101, e.g., the distance between two adjacent chambers 10 may be around 0.5 meter.

Each central ultrasonic chamber 10 may have a ring shape body mounted on external surface of conduit 101. Chamber 10 may include one or more ultrasonic transducers 11 spaced around the ring shape body of chamber 10. The ring shape body may be used to hold transducers 11 and may form together with transducers 11 and external surface of conduit 101 a confined liquid chamber which may store, hold or be filled with contact liquid to allow the propagation of the ultrasonic energy of the acoustic waves from transducers 11 through the contact liquid to the liquid flowing in conduit 101. An external surface of conduit 101 may provide acoustic coupling between the contact liquid within the liquid chamber and the liquid flowing within conduit 101. The acoustic waves may prevent formation of deposit and/or may remove deposit on internal surface of conduit 101.

According to some embodiments of the invention, side ultrasonic chambers 13 may be hermetically installed, mounted on, connected or attached to inlet 104 and/or outlet 105, located in proximity to transmissive window 103. Each side chamber 13 may have a ring shape body which may include one or more ultrasonic transducers 14 spaced around the ring shape body of chamber 13. The ring shape body may be used to hold transducers 14 which may be in direct contact with the liquid, e.g., liquid flowing into or out from conduit 101. The ultrasonic energy of the acoustic waves from transducers 14 may propagate through the walls of conduit 101 to the liquid flowing in conduit 101 and may substantially prevent formation of deposit and/or may substantially remove deposit on transmissive windows 103.

According to some embodiments of the present invention, cleaning system 15 may include one or more ultrasound generators 12 which may be coupled to or connected to transducers 11 and 14 and may generate, produce or create electric signals to vibrate transducers 11 and 14 at a desired frequency, for example, at a frequency within the range of between 20 and 100 kilohertz. Any other frequency or range of frequencies may be used.

Although in the exemplary illustrations of FIG. 1 and FIG. 2, one central ultrasonic chamber is shown, it should be understood to a person skilled in art that the invention is not limited in this respect and disinfection system 100 may include any suitable number of central ultrasonic chambers. In some embodiments, central ultrasonic chambers may be located also at the ends of conduit 101 in proximity to windows 103 as is described in detail below with reference to FIGS. 4 and 5.

Figure 3:
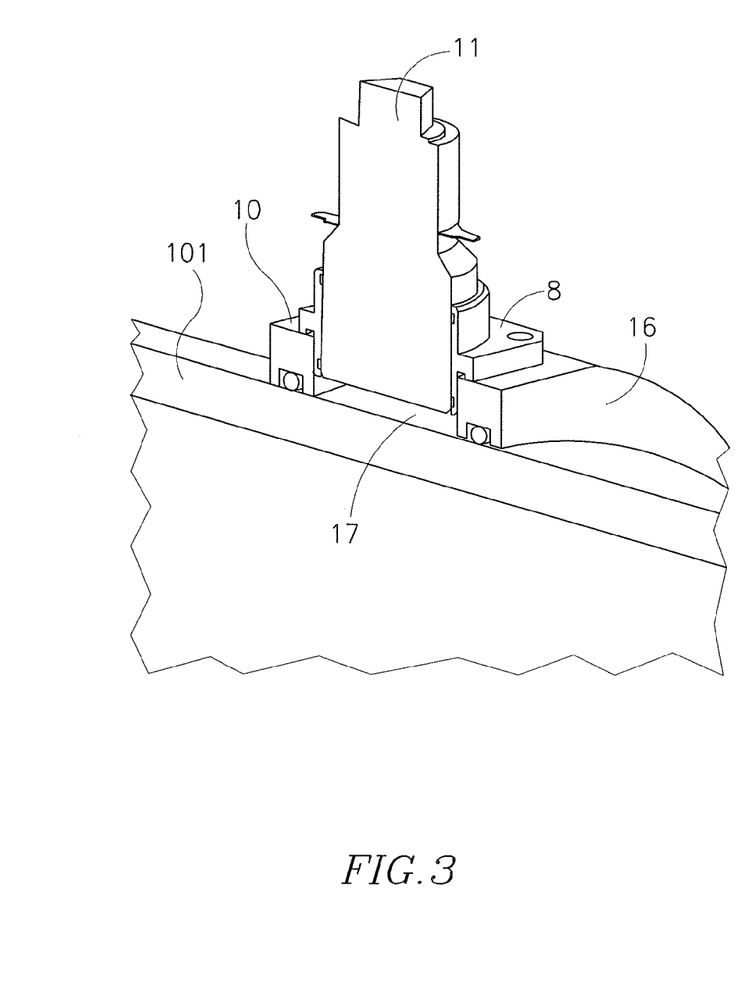
FIG. 3 is an enlarged cross section of an ultrasonic chamber of a disinfector according to some demonstrative embodiments of the invention.

Reference is now made to FIG. 3, which is an enlarged cross section of an ultrasonic chamber of a disinfector according to some demonstrative embodiments of the invention. According to some embodiments of the invention, central ultrasonic chamber 10 may contain a ring 16 hermetically mounted on the external surface of tube or conduit 101, the internal diameter of ring 16 may fit the external diameter of the tube. One or more ultrasound transducers 11 may be hermetically installed into ring 16 with an intermediate cup 8. Although the invention is not limited in this respect, ring 16 and intermediate cup 8 may be made of metal. Any other suitable material may be used. Ring 16 may carry a plurality of transducers, e.g, according to the diameter of conduit 101.

The inner surface of ring 16, the inner part of intermediate cup 8 together with the external surface of conduit 101 may form a closed volume or space 17. Space 17 may use to hold a contact liquid, for example, water, which may be used as intermediate liquid to transfer ultrasonic waves, extends from transducer 11 to the liquid to be disinfected which flows through conduit 101. The ultrasonic waves may cause the physical phenomena of cavitation inside conduit 101, e.g., in the volume of the liquid located near the internal surface of conduit 101. The cavitation may prevent formation of deposit on the walls of conduit 101 and may use to clear the inner walls of conduit 101 from already formed deposit. According to other embodiments of the invention, central ultrasonic chamber 10 may be used to prevent or remove deposit formation from windows 103 as well, as is described in detail with reference to FIGS. 4 and 5.

Figure 4:
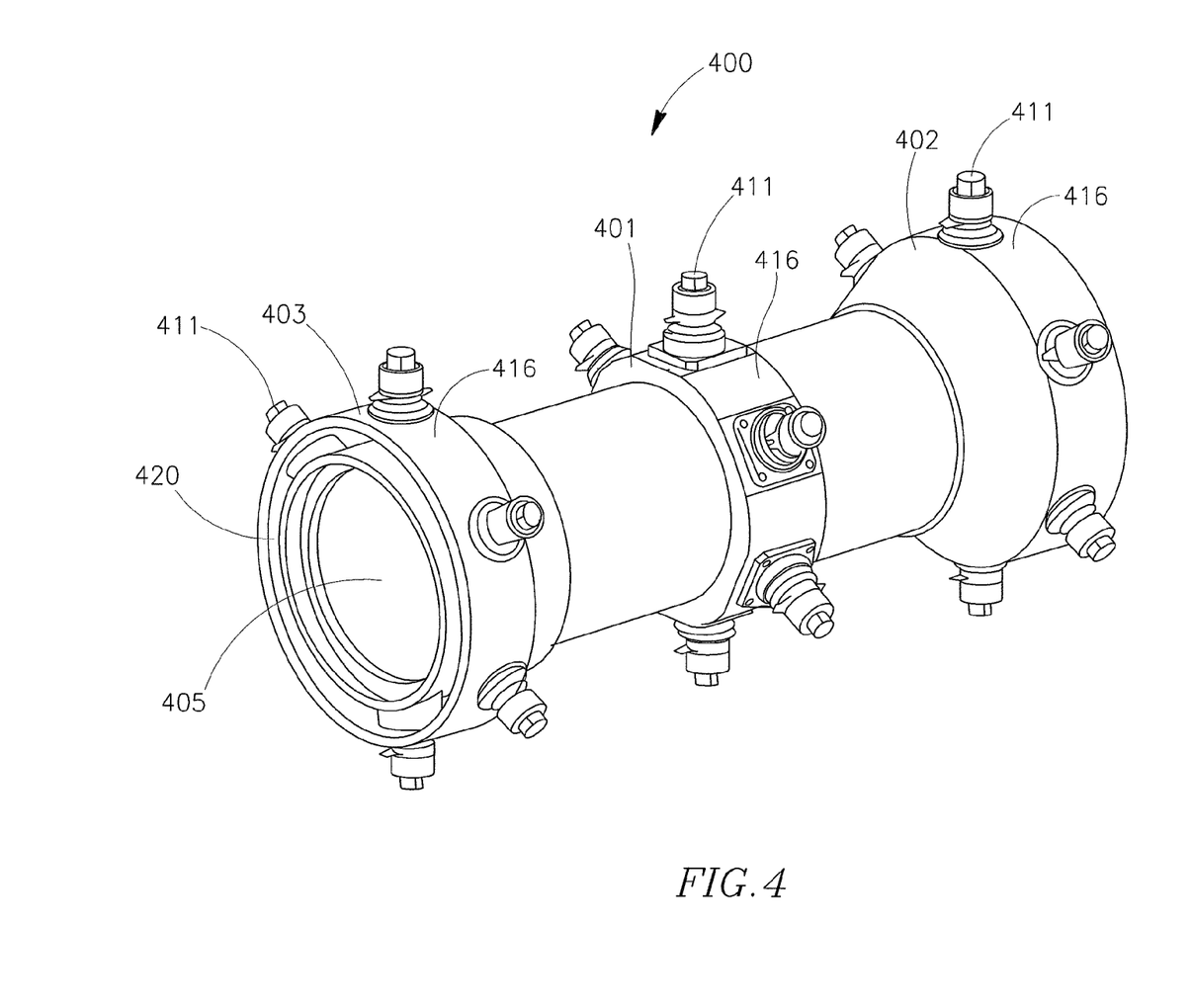
FIG. 4 is a side view of a cleaning system of a disinfector according to some embodiments of the present invention.
Figure 5:
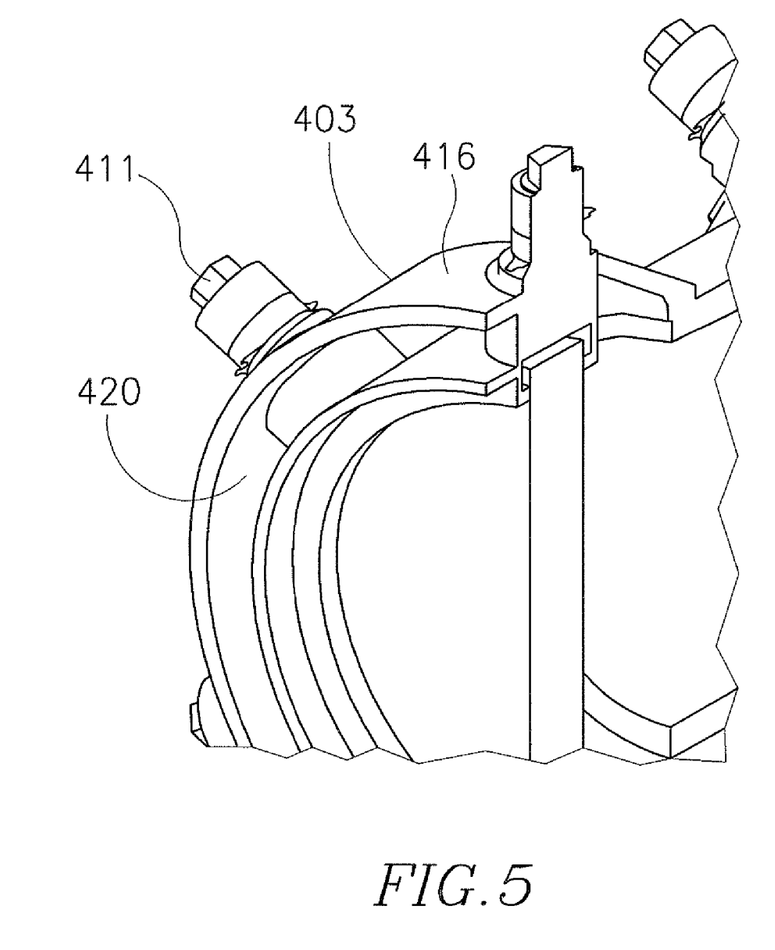
FIG. 5 is an enlarged view of a cleaning unit of the cleaning system described in FIG. 4 according to embodiments of the present invention.

Reference is now made to FIG. 4 which is a side view of a cleaning system of a disinfector according to some demonstrative embodiments of the invention and to FIG. 5 which is an enlarged view of a cleaning unit of the cleaning system of the disinfector according to some demonstrative embodiments of the invention.

According to some embodiments of the invention, cleaning system 400 may contain a plurality of cleaning units all having the same form or design, e,g, the design of central ultrasonic chambers 10 of FIG. 1. Although chamber 401 may be used for cleaning the internal walls of conduit 101 and chambers 402 and 403 may be used for cleaning the transmissive windows 405 (only one is shown), all chambers, namely chambers 401, 402 and 403 may include a ring 416 which may form a confined volume 420 to hold a contact liquid as described in detail below with reference to FIG. 1. Ring 416 may carry one or more transducer 411 which may be connected to one or more ultrasound generators (not shown). Chambers 401, 402 and 403 may be use to transfer the acoustic waves from transducer 411 through the contact liquid to the liquid entering, flowing in or exiting conduit 101.

Figure 6:
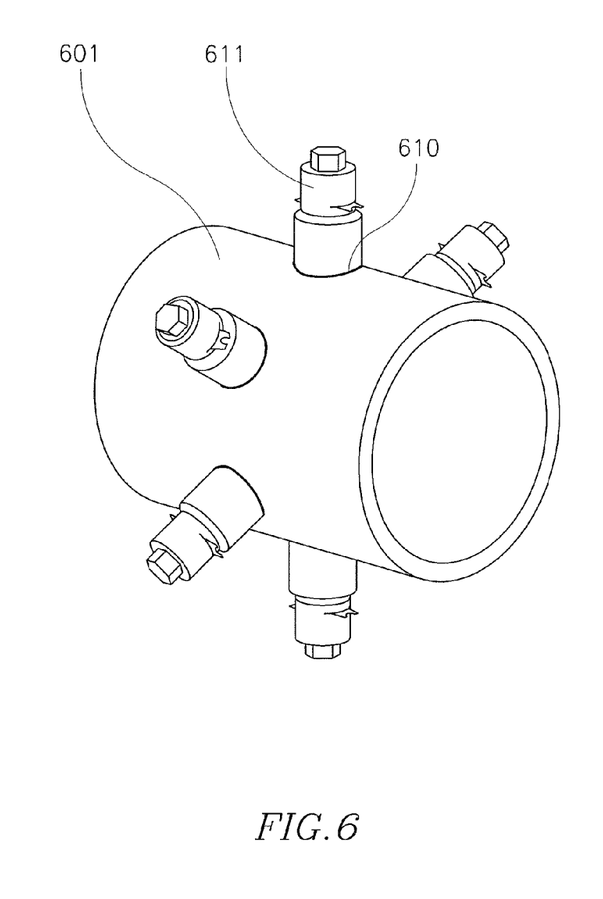
FIG. 6 is a pictorial illustration showing a cleaning system of a disinfector according to embodiments of the present invention.

Reference is now made to FIG. 6, which is a pictorial illustration showing a cleaning system of a disinfector according to some demonstrative embodiments of the invention.

According to some embodiments of the invention, one or more transducers 611 may be directly connected or pasted to conduit 601 by, for example, adhesive means 610 such as epoxy-elastic adhesive. Any other suitable adhesive or connecting means may be used. Although the invention is not limited in this respect, transducers 611 may be an integral part of conduit 601.

Ultrasonic waves may pass from transducers 611 to the liquid flowing inside conduit 601 through the walls, e,g, quarts walls of conduit 601 and may prevent and/or remove deposit formation from the inner walls of conduit 601.

Reference is now made to FIGS. 7A-7B and 8A-8B, which conceptually illustrate an exemplary disinfection system having built-in cleaning and deposit prevention capabilities according to some demonstrative embodiments of the invention. In this exemplary system, an illumination source may be located inside a transparent sleeve positioned substantially perpendicular to the longitudinal axis of symmetry of the conduit and to the direction of flow of the liquid. A disinfection system 300 may include a conduit 301 to carry liquid to be disinfected, one or more substantially UV-transparent sleeves 304 positioned within conduit 301 substantially perpendicular to its longitudinal axis of symmetry 309 and to the direction of flow of the liquid and one or more UV-radiation sources (not shown), each positioned within a respective sleeve 304. Each sleeve 304 may be attached to conduit 301 using a sleeve housing 310. The radiation source, such as a UV lamp may illuminate the liquid to be disinfected when flowing in the conduit. In this configuration, the liquid within conduit 301 may act as a waveguide and at least part of the radiation, for example, at least half of the emitted UV intensity, may be totally-internally reflected at the interface of the UV-transparent conduit 301 and the air surrounding it.

Figure 7A:
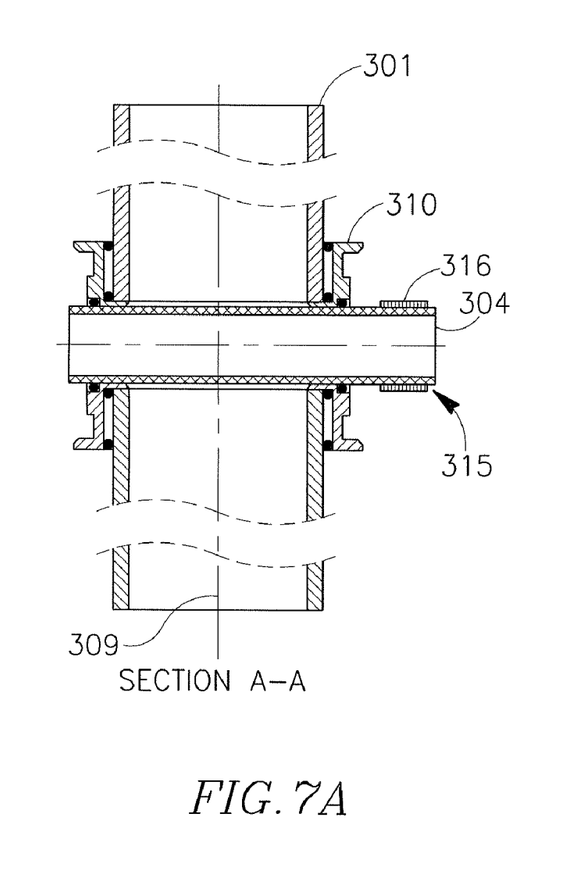
FIGS. 7A and 7B are cross section view and top view of another exemplary disinfection system having cleaning and deposit prevention capabilities according to some demonstrative embodiments of the invention.
Figure 7B:
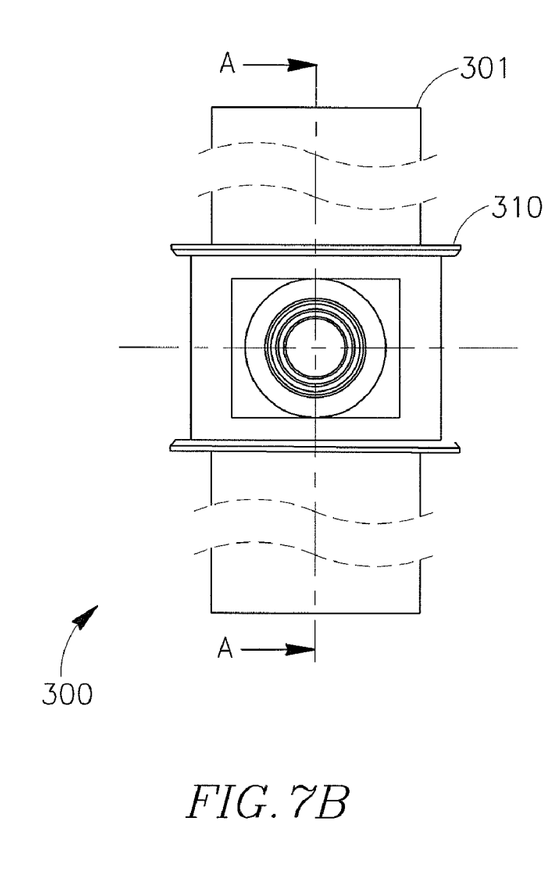
Figure 8A:
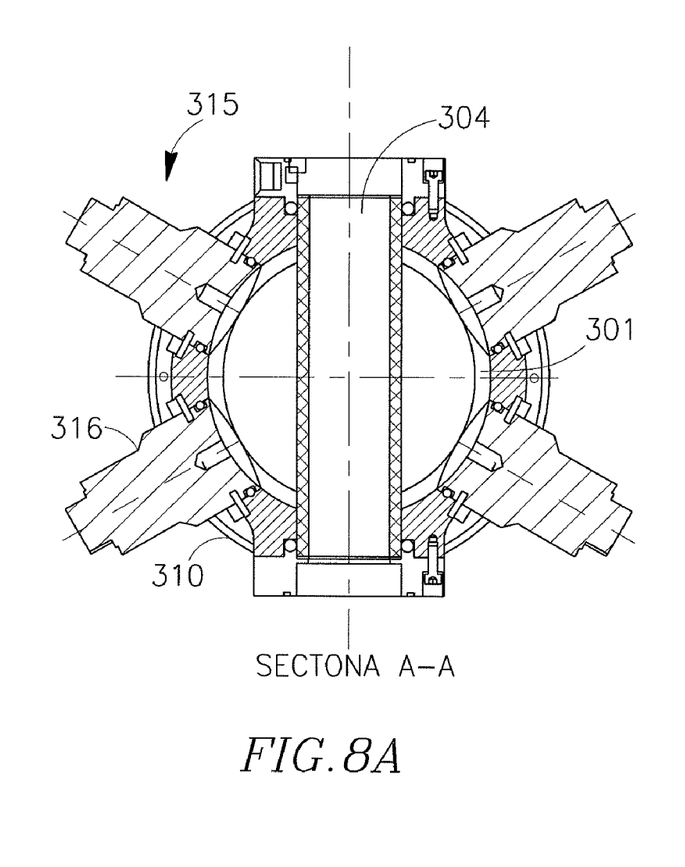
FIGS. 8A and 8B are two cross section views of an exemplary disinfection system of with a cleaning and deposit prevention unit according to some demonstrative embodiments of the invention.
Figure 8B:
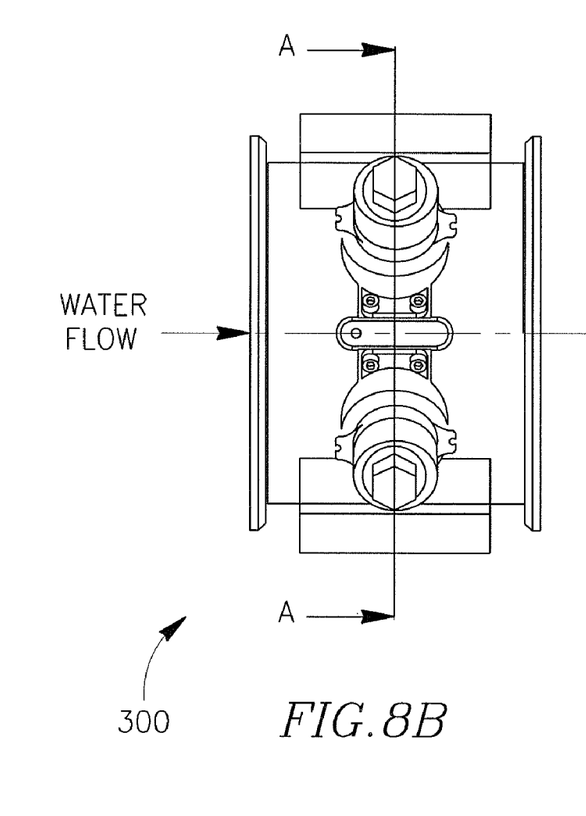

Disinfection system 300 may include an ultrasonic cleaning system 315 to prevent, decrease or treat deposit formation on various elements, such as, for example, the interior surface of conduit 301 or the external surfaces of sleeve 304. As shown in FIG. 7A, sleeve 304 may be protruded from the walls of conduit 301 and one or more ultrasonic transducers 316 may be attached to the protrusion of sleeve 304. Alternatively, as described in FIG. 7B, ultrasonic transducers 316 may be attached to housing 310.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. A system comprising:
   a conduit to carry flowing liquid to be disinfected, the conduit having an inlet portion to receive the liquid, and an outlet portion to discharge the liquid;
   an illumination source to illuminate the liquid within the conduit; and
   an ultrasonic cleaning unit to treat at least an interior surface of the conduit, wherein the ultrasonic cleaning unit includes one or more ultrasound transducers that are in direct contact with the flowing liquid within the conduit, one or more additional ultrasound transducers mounted on an external surface of the conduit and a body to hold the transducers, wherein the body forms, together with the additional transducers and an external surface of the conduit, a confined liquid chamber to store a contact liquid within which acoustic waves are generated by the additional ultrasound transducers.

2. The system of claim 1, wherein the illumination source is positioned within the conduit substantially perpendicular to the direction of flow of the liquid.

3. The system of claim 2, wherein the illumination source is positioned in a transparent sleeve.

4. The system of claim 3, wherein the sleeve is attached to the conduit by sleeve housing and the ultrasonic cleaning unit comprises one or more ultrasound transducers mounted on an external surface of the sleeve housing.

5. The system of claim 1, further comprising:
   one or more ultrasound generators coupled to the transducers to produce electric signals to vibrate the transducers at a frequency within the range of between 20 and 100 kilohertz.

6. The system of claim 1, wherein the external surface provides acoustic coupling between the contact liquid within the liquid chamber and the liquid flowing within the conduit.

7. The system of claim 1, wherein the acoustic waves substantially prevent formation of deposit on internal surfaces of the conduit.

8. The system of claim 1, wherein the acoustic waves substantially remove deposit from internal surfaces of the conduit.

9. A liquid disinfection system having built-in cleaning and deposit prevention capabilities, the system comprising:
   a conduit to carry flowing liquid to be disinfected, the conduit having an inlet portion to receive the liquid, and an outlet portion to discharge the liquid;
   an illumination source to illuminate the liquid within the conduit; and
   an ultrasonic cleaning unit to treat at least an interior surface of the conduit, wherein the ultrasonic cleaning unit includes one or more ultrasound transducers that are in direct contact with the flowing liquid within the conduit, one or more additional ultrasound transducers mounted on an external surface of the conduit and a body to hold the transducers, wherein the body forms, together with the additional transducers and an external surface of the conduit, a confined liquid chamber to store a contact liquid within which acoustic waves are generated by the additional ultrasound transducers,
   wherein the illumination source is external to the conduit, the conduit comprises a transmissive window to allow ultraviolet light from the illumination source to enter the conduit and the cleaning unit substantially prevents formation of deposit on an internal surface of the window.

10. The system of claim 1, wherein the illumination source is external to the conduit, the conduit comprises a transmissive window to allow ultraviolet light from the illumination source to enter the conduit and the cleaning unit substantially removes deposit from an internal surface of said window.

* * * * *